(12) United States Patent
Ogawa et al.

(10) Patent No.: US 11,117,895 B2
(45) Date of Patent: *Sep. 14, 2021

(54) PROCESS FOR PRODUCING CRYSTALS OF A DIAZABICYCLOOCTANE DERIVATIVE

(71) Applicant: MEIJI SEIKA PHARMA CO., LTD., Tokyo (JP)

(72) Inventors: Takaya Ogawa, Kanagawa (JP); Takuya Yokoyama, Kanagawa (JP); Shusuke Furuyama, Kanagawa (JP); Masato Ichiki, Kanagawa (JP); Kenichi Fushihara, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,550

(22) Filed: Mar. 8, 2019

(65) Prior Publication Data

US 2019/0202831 A1 Jul. 4, 2019

Related U.S. Application Data

(62) Division of application No. 15/532,281, filed as application No. PCT/JP2015/084094 on Dec. 4, 2015, now Pat. No. 10,294,224.

(30) Foreign Application Priority Data

Dec. 5, 2014 (JP) .................................. 2014-246425

(51) Int. Cl.
| | | |
|---|---|---|
| *C07D 471/08* | (2006.01) | |
| *A61K 9/19* | (2006.01) | |
| *A61K 31/439* | (2006.01) | |
| *A61K 47/02* | (2006.01) | |
| *A61K 9/00* | (2006.01) | |

(52) U.S. Cl.
CPC .......... *C07D 471/08* (2013.01); *A61K 9/0019* (2013.01); *A61K 9/19* (2013.01); *A61K 31/439* (2013.01); *A61K 47/02* (2013.01); *C07B 2200/13* (2013.01)

(58) Field of Classification Search
CPC .................................................. C07D 471/08
See application file for complete search history.

(56) References Cited

U.S. PATENT DOCUMENTS

| | | | |
|---|---|---|---|
| 5,286,856 A | 2/1994 | Kaneko et al. | |
| 5,424,069 A | 6/1995 | Kaneko et al. | |
| 6,111,098 A * | 8/2000 | Inoue .................. | C07D 477/20 540/350 |
| 7,112,592 B2 | 9/2006 | Lampilas et al. | |
| 7,612,087 B2 | 11/2009 | Aszodi et al. | |
| 7,638,529 B2 | 12/2009 | Lampilas et al. | |
| 7,732,610 B2 | 6/2010 | Lampilas et al. | |
| 8,178,554 B2 | 5/2012 | Lampilas et al. | |
| 8,288,553 B2 | 10/2012 | Priour et al. | |
| 8,471,025 B2 | 6/2013 | Dedhiya et al. | |
| 8,487,093 B2 | 7/2013 | Blizzard et al. | |
| 8,772,490 B2 | 7/2014 | Abe et al. | |
| 8,796,257 B2 | 8/2014 | Maiti et al. | |
| 8,822,450 B2 | 9/2014 | Patel et al. | |
| 8,829,191 B2 | 9/2014 | Ronsheim et al. | |
| 8,835,455 B2 | 9/2014 | Dedhiya et al. | |
| 8,877,743 B2 | 11/2014 | Maiti et al. | |
| 8,969,566 B2 | 3/2015 | Ronsheim et al. | |
| 9,006,230 B2 | 4/2015 | Bhagwat et al. | |
| 9,035,062 B2 | 5/2015 | Abe et al. | |
| 9,062,053 B2 | 6/2015 | Dedhiya et al. | |
| 9,181,250 B2 | 11/2015 | Abe et al. | |
| 9,284,273 B2 | 3/2016 | Abe et al. | |
| 9,284,314 B2 | 3/2016 | Ronsheim et al. | |
| 9,505,761 B2 | 11/2016 | Maiti et al. | |
| 9,676,777 B2 | 6/2017 | Abe et al. | |
| 9,708,320 B2 | 7/2017 | Abe et al. | |

(Continued)

FOREIGN PATENT DOCUMENTS

| | | |
|---|---|---|
| EP | 0213595 | 3/1987 |
| EP | 0533149 A1 | 3/1993 |

(Continued)

OTHER PUBLICATIONS

Matthew L. Peterson et. al. "Expanding the Scope of Crystal Form Evaluation in Pharmaceutical Science" Journal of Pharmacy & Pharmaceutical Science 2006 (9(3):317-326.*

Miller et. al. "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.*

U.S. Appl. No. 15/613,620; First Named Inventor: Takao Abe; Title: "Process for Producing Diazabicyclooctane Derivative", filed Jun. 5, 2017.

Brown et al, "Some Active Derivatives of Penicillin", Applied Microbiology 1969, vol. 17, No. 3, pp. 339-343.

(Continued)

*Primary Examiner* — David K O'Dell

(74) *Attorney, Agent, or Firm* — Holtz, Holtz & Volek PC

(57) ABSTRACT

A process for producing crystals of a compound represented by the following formula (I):

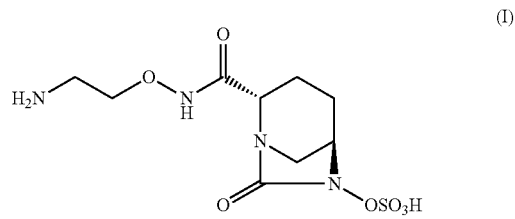

by crystallizing the compound from an aqueous solution containing the compound and an inorganic salt, such as sodium chloride. Such crystals can be subjected to lyophilization to provide a lyophilized composition having a desirable storage stability.

5 Claims, 3 Drawing Sheets

(56) References Cited

U.S. PATENT DOCUMENTS

| | | | |
|---|---|---|---|
| 10,000,491 B2 | 6/2018 | Abe et al. | |
| 10,000,492 B2 | 6/2018 | Abe et al. | |
| 10,023,573 B2 | 7/2018 | Abe et al. | |
| 10,131,665 B2 | 11/2018 | Abe et al. | |
| 10,294,224 B2* | 5/2019 | Ogawa | A61K 31/439 |
| 10,556,905 B2 | 2/2020 | Abe et al. | |
| 10,604,522 B2 | 3/2020 | Abe et al. | |
| 2003/0199541 A1 | 10/2003 | Lampilas et al. | |
| 2003/0220521 A1 | 11/2003 | Reitz et al. | |
| 2005/0020572 A1 | 1/2005 | Aszodi et al. | |
| 2005/0245505 A1 | 11/2005 | Aszodi et al. | |
| 2006/0046995 A1 | 3/2006 | Lampilas et al. | |
| 2006/0189652 A1 | 8/2006 | Lampilas et al. | |
| 2007/0299108 A1 | 12/2007 | Aszodi et al. | |
| 2009/0215747 A1 | 8/2009 | Aszodi et al. | |
| 2010/0048528 A1 | 2/2010 | Aszodi et al. | |
| 2010/0087648 A1 | 4/2010 | Lampilas et al. | |
| 2010/0197928 A1 | 8/2010 | Priour et al. | |
| 2011/0021772 A1 | 1/2011 | Lampilas et al. | |
| 2011/0046102 A1 | 2/2011 | Ledoussal et al. | |
| 2011/0152311 A1 | 6/2011 | Dedhiya et al. | |
| 2011/0213147 A1 | 9/2011 | Lampilas et al. | |
| 2011/0245254 A1 | 10/2011 | Aszodi et al. | |
| 2011/0294777 A1 | 12/2011 | Blizzard et al. | |
| 2012/0053350 A1 | 3/2012 | Mangion et al. | |
| 2013/0012712 A1 | 1/2013 | Priour et al. | |
| 2013/0225554 A1 | 8/2013 | Maiti et al. | |
| 2013/0267480 A1 | 10/2013 | Dedhiya et al. | |
| 2013/0274475 A1 | 10/2013 | Mangion et al. | |
| 2013/0281359 A1 | 10/2013 | Maiti et al. | |
| 2014/0221341 A1 | 8/2014 | Maiti et al. | |
| 2014/0288051 A1 | 9/2014 | Maiti et al. | |
| 2014/0303375 A1 | 10/2014 | Abe et al. | |
| 2015/0141401 A1 | 5/2015 | Abe et al. | |
| 2015/0239840 A1 | 8/2015 | Abe et al. | |
| 2015/0246920 A1 | 9/2015 | Dedhiya et al. | |
| 2016/0024090 A1 | 1/2016 | Abe et al. | |
| 2016/0137645 A1 | 5/2016 | Abe et al. | |
| 2016/0264573 A1 | 9/2016 | Abe | |
| 2016/0272641 A1 | 9/2016 | Abe et al. | |
| 2017/0233393 A1 | 8/2017 | Abe et al. | |
| 2017/0283415 A1 | 10/2017 | Abe et al. | |
| 2017/0327499 A1 | 11/2017 | Ogawa et al. | |
| 2018/0258089 A1 | 9/2018 | Abe et al. | |
| 2019/0031659 A1 | 1/2019 | Abe et al. | |
| 2020/0048253 A1 | 2/2020 | Abe et al. | |
| 2020/0181143 A1 | 6/2020 | Abe et al. | |

FOREIGN PATENT DOCUMENTS

| | | |
|---|---|---|
| GB | 1589317 A | 5/1981 |
| JP | 60019759 B2 | 6/1979 |
| JP | 03074643 B2 | 11/1991 |
| JP | 2767171 B2 | 6/1998 |
| JP | 2843444 B2 | 1/1999 |
| JP | 2004505088 A | 2/2004 |
| JP | 2005518333 A | 6/2005 |
| JP | 2005523897 A | 8/2005 |
| JP | 2010138206 A | 6/2010 |
| JP | 4515704 B2 | 8/2010 |
| JP | 2010539147 A | 12/2010 |
| JP | 2011510012 A | 3/2011 |
| JP | 2011518871 A | 6/2011 |
| JP | 2011207900 A | 10/2011 |
| JP | 2012504593 A | 2/2012 |
| JP | 5038509 B2 | 10/2012 |
| WO | 9529913 A1 | 11/1995 |
| WO | 0210172 A1 | 2/2002 |
| WO | 02100860 A2 | 12/2002 |
| WO | 03063864 A2 | 8/2003 |
| WO | 2009090320 A1 | 7/2009 |
| WO | 2009091856 A2 | 7/2009 |
| WO | 2009133442 A1 | 11/2009 |
| WO | 2010038115 A1 | 4/2010 |
| WO | 2010126820 A2 | 11/2010 |
| WO | 2011042560 A1 | 4/2011 |
| WO | 2012086241 A1 | 6/2012 |
| WO | 2012172368 A1 | 12/2012 |
| WO | 2013030735 A1 | 3/2013 |
| WO | 2013038330 A1 | 3/2013 |
| WO | 2013180197 A1 | 12/2013 |
| WO | 2015046207 A1 | 4/2015 |
| WO | 2015053297 A1 | 4/2015 |

OTHER PUBLICATIONS

Witkop, et al., "The Configuration of 5-Hydroxypipecolic Acid from Dates", Journal of the American Chemical Society, Jan. 5, 1957, vol. 79, No. 1, pp. 192-197.

Extended European Search Report (EESR) dated Apr. 3, 2018 issued in counterpart European Application No. 15866317.9.

Walker, "The Management of Chemical Process Development in the Pharmaceutical Industry", 2008, John Wiley & Sons, p. 186.

Teruzo, "Solvent Handbook", Incorporated Company Kodansha, 1985: pp. 47-51.

Flow of research of Ryuichi Kato and optical isomerism medicine, Time Signal Company, Oct. 1, 1987, 29th volume, No. 10: pp. 2039-2042.

In edited by Chemical Society of Japan, "4th Edition Experimental Science Lecture 1 basic operation I", The Maruzen Co., Ltd: pp. 184-189.

International Search Report (ISR) and Written Opinion dated Mar. 8, 2016 issued in International Application No. PCT/JP2015/084094.

Tidwell, "Sulfur Trioxide-Pyridine", Encyclopedia of Reagents for Organic Synthesis, vol. 7, Edited by Leo A Paquette, 1995, John Wiley and Sons, pp. 4703-4704.

Rowe, "Handbook of Pharmaceutical Excipients", 5th Edition 2006, pp. 671-672.

Pettit, et al., "8-Hydroxy-5-trifluoromethylquinoline", Journal of Chemical Society (1954), 3852-3854.

Nohira, "Agricultural chemicals, medicine, optically active substance, The organic industrial chemistry", Asakura Publishing Co.,Ltd., Jan. 20, 1989, 1st printing: pp. 20, 21.

Japanese Office Action dated Sep. 12, 2017 which issued in Japanese Application No. 2014-518712.

Korey et al., "Effects of exipients on the crystallisation of pharmaceutical compounds during lyophilization", Journal of Parental Science and Technology, vol. 43, Mar. 1989 (Mar. 1989), pp. 80-83.

Mangion et al, "A Concise Synthesis of a β-Lactamase Inhibitor", Organic Letters, 2011, vol. 13, No. 20, pp. 5480-5483.

Noriaki Hirayama, et al, "Yuki Kagobutsu Kessho Sakusei Handbook—Genii to Know How-," Maruzen Co., Ltd., Jul. 25, 2008, pp. 57-84.

Yamanaka, et al., "The Preparation, bioactive and use of an optically active substance, Quarterly Chemistry Survey—Separation of an optical isomer", Japan Scientific Societies Press, Inc., Jun. 10, or 1989, No. 6: pp. 8-9,124, 212-213.

Merriam Webster, "Alternate/Alternately", Merriam Webster Online Dictionary, Jul. 17, 2018, XP55493061, <https://www.merriamwebster.com/dictionary/alternately>.

U.S. Appl. No. 14/872,988, Title: "Beta-Lactamase Inhibitor and Process for Preparing the Same", filed Oct. 1, 2015, First Named Inventor: Takao Abe.

U.S. Appl. No. 15/007,906, Title: "Compounds Useful for Producing an Optically Active Diazabicyclooctane Compound", filed Jan. 27, 2016, First Named Inventor: Takao Abe.

U.S. Appl. No. 15/023,976, Title: "Process for Producing Diazabicyclooctane Derivative and Intermediate Thereof", filed Mar. 22, 2016, First Named Inventor: Takao Abe.

U.S. Appl. No. 15/027,956; First Named Inventor: Takao Abe; Title: "Crystalline Forms of Diazabicyclooctane Derivative and Production Process Thereof", filed Apr. 7, 2016.

Baldwin, et al., "A Novel Entry to Carbenoid Species via β-Ketosulfoxonium Ylides", Journal of the Chemical Society, Chemical Communications, 1993, pp. 1434-1435.

Caira, "Crystalline Polymorphism of Organic Compounds", Topics in Current Chemistry, Springer, Berlin, DE, vol. 198, Jan. 1, 1998: pp. 163-208.

(56) References Cited

OTHER PUBLICATIONS

Cerfontain, et al., "Sulfur Trioxide", Encyclopedia of Reagents for Organic Synthesis, vol. 7, edited by Leo A. Paquette, 1995, John Wiley and Sons, pp. 4699-4702.
Dolence, et al., "Synthesis and Siderophore Activity of Albomycin-like Peptides Derived from N5-Acetyl-N5-hydroxy-L-ornithine", Journal of Medicinal Chemistry, 1991, vol. 34, No. 3, pp. 956-968.
Freed, et al., "Synthesis of 5-Ketopipecolic Acid from Glutamic Acid", The Journal of Organic Chemistry, Dec. 1960, vol. 25, No. 12, pp. 2105-2107.
Hirayama, "Organic compound crystal production handbooks", 2008: pp. 17-23, 37-40, 45-51, 57-65.
Jung, et al., "Diastereoselective synthesis of (2S,5S)- and (2S,5R)-N-benzyloxycarbonyl-5-hydroxypipecolic acids from trans-4-hydroxy-L-proline", Tetrahedron: Asymmetry 17 (2006), pp. 2479-2486.
King, et al., "The Chemistry of Extractives from Hardwoods. Part III. Baikiain, an Amino-acid Present in Baikiaea plurijuga", Journal of the Chemical Society, 1950, pp. 3590-3597.
Knight, "N-Hydroxysuccinimide", Encyclopedia of Reagents for Organic Synthesis, vol. 4, Edited by Leo A. Paquette, 1995, John Wiley and Sons, pp. 2780-2781.
Merriam Webster, "Alternative/Alternatively", Merriam Webster Online Dictionary, Jul. 17, 2018, XP55493064, <https://www.merriam-webster.com/dictionary/alternatively.
Mangion, et al., "Iridium-Catalyzed X-H Insertions of Sulfoxonium Ylides", Organic Letters, 2009, vol. 11, No. 16, pp. 3566-3569.
Mcintosh, "Sulfur Troxide-1, 4-Dioxane", Encyclopedia of Reagents for Organic Synthesis, vol. 7, Edited by Leo A. Paquette, 1995, John Wiley and Sons, pp. 4702-4703.
Israeli Office Action dated Nov. 28, 2019 issued in Israeli Application No. 252691.
"Polymorphism in Pharmaceutical Solids", Drugs and the Pharmaceutical Sciences, vol. 95, Edited by H. G. Brittain. Chapter 1, by D.J.W. Grant, pp. 1-10; Chapter 5 by J.K. Guillory; pp. 183-226; Dec. 31, 1999.
Office Action (Non-Final Rejection) dated Feb. 5, 2021 issued in related U.S. Appl. No. 16/660,682.

\* cited by examiner

PROCESS FOR PRODUCING CRYSTALS OF A DIAZABICYCLOOCTANE DERIVATIVE

CROSS-REFERENCE TO RELATED APPLICATIONS

This application is a Divisional application of U.S. application Ser. No. 15/532,281, filed Jun. 1, 2017, which is a U.S. National Phase application of International Application No. PCT/JP2015/084094, filed Dec. 4, 2015, which is based upon and claims the benefit of priority from prior Japanese Patent Application No. 2014-246425, filed Dec. 5, 2014. The entire contents of all the above-identified applications are incorporated herein by reference.

TECHNICAL FIELD

The present invention relates to a process for producing crystals of a diazabicyclooctane derivative represented by formula (I), as well as a composition and lyophilized preparation of said derivative, and a process for producing the same.

BACKGROUND

The novel diazabicyclooctane derivative represented by formula (I) below: (2S,5R)—N-(2-aminoethoxy)-7-oxo-6-(sulfooxy)-1,6-diazabicyclo [3.2.1]octane-2-carboxamide (hereinafter referred to as "Compound (I)") is a β-lactamase inhibitor, and disclosed in WO2013/180197 (Patent Document 1).

[Chemical formula 1]

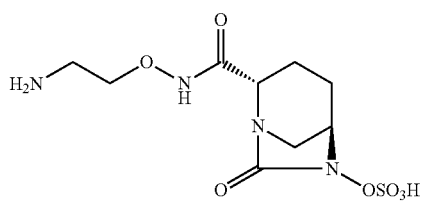

(I)

A method for obtaining a crystalline lyophilized composition has been disclosed in which a solution of a chemical substance is frozen at a prescribed temperature, and heated to a prescribed temperature, after which the temperature is kept constant (hereafter referred to as a heat treatment step) (Patent Document 2).

Patent Document 3 and Patent Document 4 disclose that an inorganic salt may be added to an solution of a chemical substance in lyophilization methods that involve a heat treatment step.

Patent Document 5 discloses a method for obtaining a crystalline lyophilized composition by subjecting an aqueous solution of a chemical substance containing 2 to 10% (v/v) of a $C_{1-3}$ alcohol or acetone to a lyophilization procedure that involves a heat treatment step.

Patent Document 6 discloses crystals of compound (I) and production process thereof.

PRIOR ART DOCUMENTS

Patent Documents

[Patent Document 1] WO2013/180197
[Patent Document 2] Japanese Examined Patent Publication No. Hei 03-74643
[Patent Document 3] Japanese Patent No. 2843444
[Patent Document 4] Japanese Patent No. 2767171
[Patent Document 5] Japanese Examined Patent Publication No. Sho 60-19759
[Patent Document 6] WO 2015/053297

SUMMARY OF THE INVENTION

Problems to be Solved by the Invention

Our studies have shown that when compound (I) is lyophilized using standard conditions that include a freezing step, followed by a step of drying under reduced pressure, compound (I) becomes amorphous, and that its chemical stability is significantly lower than the crystalline state, making it difficult to obtain a lyophilized composition having good storage stability. In light of producing and distribution, a stable lyophilized composition of compound (I) has been highly sought after.

However, lyophilization of an aqueous solution of compound (I) using the method of Patent Document 2 did not yield a crystalline lyophilized composition. The examples of Patent Document 3 show that a crystalline lyophilized composition can be obtained whether or not an inorganic salt is added, which means that addition of an inorganic salt is not essential for crystallization. Moreover, it is disclosed that, under standard lyophilization conditions that involve no heat treatment step, addition of an inorganic salt leads to an increase in amorphous content, thereby adversely affecting crystallization. Furthermore, in Patent Document 4, a heat treatment step is incorporated without exception and there are no examples where an inorganic salt is added. The method of Patent Document 5 is not desirable as an industrial producing process, as there is concern over residual solvents.

As seen from the above, no methods have been found for obtaining a crystalline lyophilized composition under lyophilization conditions that do not involve a heat treatment step or addition of an organic solvent.

On the other hand, the process of Patent Document 6 could not provide crystals of compound (I) sufficiently before an aqueous solution containing compound (I) is purified once by a column and the like.

Further, it is problem to obtain a single crystalline form and in particular stable form I by controlling polymorphism.

Therefore, a process for producing crystals of compound (I) easily in an industrial scale, and further a process for producing a single crystalline form and in particular crystalline form I of compound (I) has been highly sought after.

The objects of the present invention are to provide a process for producing crystals, especially a single crystalline form and in particular stable crystalline form I of compound (I) easily in an industrial scale, and a stable lyophilized composition of compound (I).

Means for Solving the Problems

As a result of extensive research on developing a lyophilized composition of compound (I) having good storage stability, the present inventor has found that subjecting an aqueous solution containing compound (I) and an inorganic salt such as sodium chloride to lyophilization crystallizes the compound (I), and consequently yields a lyophilized composition having good storage stability wherein the compound (I) is crystalline, especially a single crystalline form and in particular stable crystalline form I, and has further found that crystals, especially a single crystalline form and in particular stable crystalline form I of compound (I) can be obtained from said aqueous solution without lyophilization, thereby completing the present invention.

The present invention relates to a process for producing crystals of compound (I), comprising crystallizing compound (I) from an aqueous solution containing compound (I) and an inorganic salt such as sodium chloride.

The present invention also relates to a process for producing a lyophilized composition comprising compound (I), comprising crystallizing compound (I) by said process for producing crystals of compound (I); a process for producing a lyophilized composition comprising compound (I), comprising crystallizing compound (I) by subjecting an aqueous solution containing compound (I) and an inorganic salt such as sodium chloride to lyophilization; as well as a lyophilized composition containing crystals of compound (I) and an inorganic salt such as sodium chloride. The lyophilized composition of the present invention is obtainable by said process for producing a lyophilized composition.

In the present invention, for example, compound (I) is crystallized by a general method including a method wherein a seed crystal is added as necessary to an aqueous solution containing compound (I) and an inorganic salt such as sodium chloride, and then a poor solvent is added thereto. Or, compound (I) is crystallized by subjecting an aqueous solution containing compound (I) and an inorganic salt such as sodium chloride to lyophilization. The presence of an inorganic salt such as sodium chloride allows crystals of compound (I), especially, same crystalline form I as one disclosed in Patent Document 6 to be obtained, thereby drastically improving storage stability compared to amorphous states.

Crystalline form I of the present invention is the same as crystalline form I of Patent Document 6, and shows a characteristic peak pattern in powder X-ray diffraction as shown in Table 1 and FIG. 3 below. In the present invention, the powder X-ray diffraction is measured according to a method mentioned in Test example 1.

TABLE 1

Powder X-ray data
Powder X-ray diffraction of Crystalline form I

| 2θ (CuKα) | Latticer spacing (d) Å | Relative intensity I/IO |
|---|---|---|
| 12.04 | 7.34 | 13 |
| 15.64 | 5.66 | 53 |
| 16.02 | 5.53 | 26 |
| 16.70 | 5.30 | 58 |
| 17.66 | 5.02 | 49 |
| 19.02 | 4.66 | 100 |
| 20.30 | 4.37 | 46 |
| 20.74 | 4.28 | 11 |
| 21.88 | 4.06 | 10 |
| 24.16 | 3.68 | 11 |
| 24.56 | 3.62 | 15 |
| 25.66 | 3.47 | 18 |
| 26.54 | 3.36 | 17 |
| 26.96 | 3.30 | 13 |

TABLE 1-continued

Powder X-ray data
Powder X-ray diffraction of Crystalline form I

| 2θ (CuKα) | Latticer spacing (d) Å | Relative intensity I/IO |
|---|---|---|
| 28.18 | 3.16 | 12 |
| 28.72 | 3.11 | 14 |
| 29.44 | 3.03 | 16 |
| 29.86 | 2.99 | 13 |
| 35.90 | 2.50 | 10 |

Further, in the present invention, an aqueous solution containing compound (I) and an inorganic salt such as sodium chloride is subjected to lyophilization. For example, it is lyophilized using standard conditions that include a freezing step, and a subsequent step of drying under reduced pressure. That is, the present invention also relates to a process for producing a lyophilized composition comprising compound (I), comprising subjecting an aqueous solution containing compound (I) and an inorganic salt such as sodium chloride to a freezing step, and subjecting a frozen product obtained in said freezing step to a step of drying under reduced pressure. The presence of an inorganic salt such as sodium chloride allows a lyophilized composition to be obtained wherein the compound (I) is crystalline and especially crystalline form I, thereby drastically improving storage stability compared to amorphous states.

In the present invention, a lyophilized composition wherein the compound (I) is crystalline can be obtained without involving a heat treatment step or a refreezing step between the steps of freezing and drying under reduced pressure. That is, in the process of the present invention for producing a lyophilized composition, no heat treatment or refreezing of a frozen product obtained in said freezing step may be performed. In general, lyophilization is a producing process that requires a long time. Methods are known for obtaining a crystalline lyophilized composition that involve a heat treatment step and a refreezing step between the steps of freezing and drying under reduced pressure, but there is a problem of low productivity due to further extended producing times. In the present invention, a lyophilized composition wherein the compound (I) is crystalline can be obtained without involving a heat treatment step or a refreezing step between the steps of freezing and drying under reduced pressure, thereby increasing productivity compared to conventional methods.

In the present invention, a heat treatment step and a refreezing step may be incorporated between the steps of freezing and drying under reduced pressure. That is, the present invention also relates to said process for producing a lyophilized composition comprising compound (I), further comprising subjecting the frozen product obtained in said freezing step to a heat treatment step, subjecting a heat-treated product obtained in said heat treatment step to a refreezing step, and subjecting a refrozen product obtained in said refreezing step to said step of drying under reduced pressure. The incorporation of a heat treatment step further improves the crystallization efficiency of compound (I).

Effects of Invention

In the present invention, crystals of compound (I) can be obtained by crystallization from an aqueous solution containing compound (I) and an inorganic salt without previous purification of compound (I) with a column, etc., and thus, crystals, especially a single crystalline form and in particular stable crystalline form I of compound (I) can be predominantly produced easily in an industrial scale. Further, in the present invention, a lyophilized composition wherein compound (I) is crystalline, especially a single crystalline form and in particular crystalline form I can be obtained by lyophilization from an aqueous solution containing compound (I) and an inorganic salt, and then a lyophilized preparation of compound (I) having good storage stability can be provided.

BRIEF DESCRIPTION OF DRAWINGS

FIG. 1 Powder X-ray diffractogram of the lyophilized composition obtained in Example 1a.

MODE FOR CARRYING OUT THE INVENTION

Figure 1:
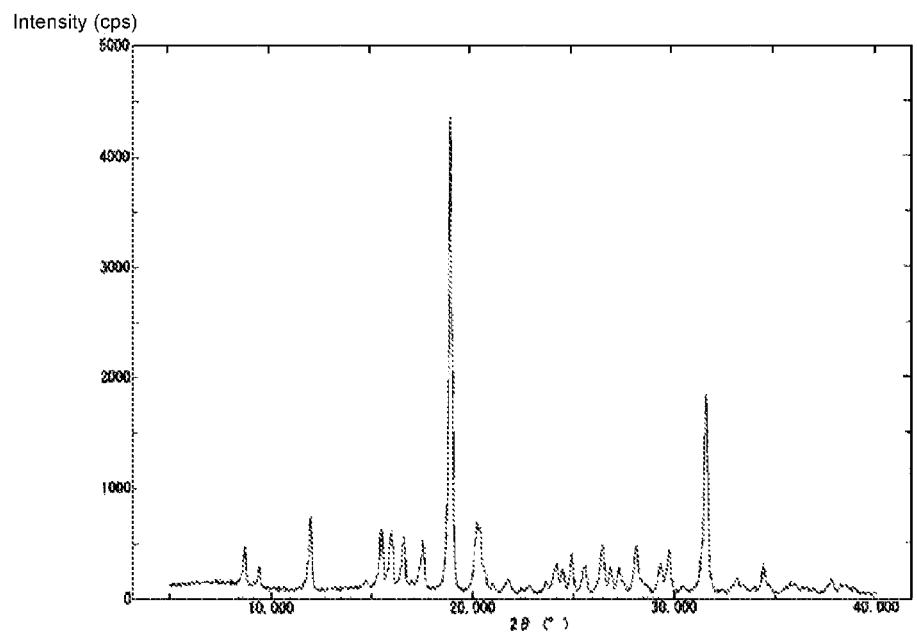

Any inorganic salt that can be added to a parenteral injection may be used in the present invention, and sodium chloride, magnesium chloride, calcium chloride, potassium chloride, ammonium chloride, sodium bromide, calcium bromide, potassium bromide, tetrabutyl ammonium bromide, magnesium sulfate, sodium iodide, potassium iodide, sodium hydrogenphosphate, sodium acetate, sodium citrate, sodium tartrate, sodium glutamate, Rochelle salt (potassium sodium tartrate), etc. are exemplified. Sodium chloride, magnesium chloride, magnesium sulfate, sodium citrate, sodium glutamate and Rochelle salt (potassium sodium tartrate) are preferable in terms of crystallization efficiency. It was confirmed that crystalline form I of compound (I) can be obtained by using any of these inorganic salts. Sodium chloride is particularly preferable. The amount of the inorganic salt of the present invention contained in a lyophilized composition or a medicinal preparation may vary, but is preferably 0.1 to 10 molar equivalents, and more preferably 1 to 2 molar equivalents to compound (I). This is because adding the amount that is too large or too small would result in a decrease in crystallization efficiency, and affect the stability of the preparation.

Further, in case of crystallization from an aqueous solution containing compound (I) and an inorganic salt, the amount of the inorganic salt contained in said aqueous solution may vary, but is preferably 0.1 to 10 molar equivalents, and more preferably 0.5 to 1.5 molar equivalents to compound (I).

In the present invention, the concentration of compound (I) in the aqueous solution prior to crystallization or lyophilization is typically 1 to 40% (w/w), preferably 2.5 to 20% (w/w), and more preferably 7.5 to 10% (w/w). This is because low said concentrations lead to a decrease in crystallization efficiency, thereby affecting the stability of the preparation, whereas high said concentrations are prone to precipitation from oversaturated solutions.

An aqueous solution containing compound (I) and an inorganic salt of the present invention may be prepared by dissolving compound (I) and an inorganic salt together in water, or by dissolving either of them in water to provide a solution, and then dissolving the residual other in the solution In the present invention, for example, compound (I) is crystallized by adding a seed crystal as necessary to an aqueous solution containing compound (I) and an inorganic salt, and then adding a poor solvent thereto. Here, as the seed crystal, seed crystals of compound (I) may be used, for example, crystalline forms I of Patent Document 6 may be used. Or, a lyophilized composition obtained by subjecting an aqueous solution containing compound (I) and an inorganic salt to lyophilization may be used as the seed crystal. The amount of the seed crystal used is 0 to 20 wt % and preferably 0.01 to 2 wt %.

Examples of poor solvents include alcohol such as methanol, ethanol 1-propanol and isopropanol, acetone, acetonitrile, and tetrahydrofuran, and preferably include alcohol such as methanol, ethanol, 1-propanol or isopropanol. The amount of the poor solvent is adjusted based on solubility so that isolation loss is 1% or less. For example, the poor solvent is used at 1 to 10 times, preferably 3 to 7.5 times and more preferably 5 to 7.5 times, the initial volume of the aqueous solution containing compound (I) and an inorganic salt. The timing of the addition of poor solvent is not limited. For example, after the mixture has formed slurry following seeding, the poor solvent is dropped therein in the case of crystalline form I. Time for the addition of poor solvent is not limited, and for example, half an hour or more, and preferably one hour or more.

In the present invention, compound (I) may be crystallized after control of the temperature of an aqueous solution containing compound (I) and an inorganic salt.

Stirring time is dependent upon precipitation rate, and stirring is carried out for 1 hour to 24 hours and preferably for 1 hour to 15 hours.

The crystals of compound (I) can be obtained by ordinary filtration, washing and through-flow drying or vacuum drying of the precipitated crystals. In the case of solvated crystals, excessive drying is avoided by using means to controlling material temperature, loss on drying, humidified and limited vacuum drying or humidified through-flow drying.

In the present invention, compound (I) may be crystallized by subjecting an aqueous solution containing compound (I) and an inorganic salt to lyophilization. Further, the present invention also relates to a process for producing a lyophilized composition comprising compound (I), comprising crystallizing compound (I) by subjecting an aqueous solution containing compound (I) and an inorganic salt to lyophilization.

In the present invention, for example, an aqueous solution containing compound (I) and an inorganic salt is subjected to a conventional lyophilization procedure that includes a freezing step and a step of drying under reduced pressure. The refrigeration temperature used for freezing said aqueous solution varies depending on the concentrations of compound (I) and the inorganic salt, but is typically between −60 and −10° C., preferably between −50 and −10° C., more preferably between −50 and −15° C. The rate used for freezing may vary, but the freezing step typically lasts for 0.25 to 5 hours. After freezing, the frozen product obtained in the freezing step may be stored at the refrigeration temperature for a period of time until the next step of drying under reduced pressure.

The step of drying under reduced pressure to which the frozen product obtained in said freezing step is subjected may be divided into a step of primary drying (sublimation)

and a step of secondary drying (dehumidification). The primary drying step is performed, as is typical, under reduced pressure, and although the temperature to be used cannot be specified because it is affected by the concentrations of compound (I) and an inorganic salt, it is preferably adjusted to conditions in which the temperature of the material does not exceed the collapse temperature of the frozen product. The drying time cannot be specified because it varies depending on the temperature used and the scale of production, but this step may typically last for 2 hours to 7 days, preferably 5 hours to 72 hours, while changes in the temperature of the material and the degree of vacuum are monitored. The secondary drying step is performed, as is typical, under reduced pressure and it may be performed at a temperature of, for example, 10 to 60° C., preferably 25 to 60° C. The drying time cannot be specified because it varies depending on the temperature used and the scale of production, but this step may typically last for 2 to 72 hours, preferably 5 to 20 hours, while changes in the temperature of the material and the degree of vacuum are monitored.

In the present invention, to improve crystallization efficiency, a heat treatment step and a refreezing step may be incorporated between the freezing step and the step of drying under reduced pressure, which are described above. The temperature used in heat treatment of the frozen product obtained in said freezing step is affected by the concentrations of compound (I) and an inorganic salt, but this step is performed at a temperature where the material remains frozen, preferably at −40 to 0° C., and more preferably −20 to −4° C. The heat treatment time cannot be specified because it varies depending on the temperature used and the scale of production, but this step may typically last for 0.5 to 72 hours, preferably 1 to 24 hours. The temperature used in the refreezing step to which a heat-treated product obtained in said heat treatment step is subjected is typically −60 to −10° C., preferably −50 to −10° C., more preferably −50 to −15° C. The freezing rate may vary, but this step typically lasts for 0.25 to 5 hours. A refrozen product obtained in the refreezing step is subjected to said step of drying under reduced pressure.

When the crystals and the lyophilized compositions of the present invention are used as a medicament, they may be administered as such (as ingredients), or may be administered as a conventional medicinal preparation. Said medicinal preparation may contain a pharmacologically acceptable additive such as excipient, lubricant, binder, disintegrant, emulsifier, stabilizer, flavoring agent, diluent or the like, so long as the additive do not undermine the effects of the present invention. Examples of said medicinal preparation include tablets, capsules, powders, syrups, granules, fine granules, pills, suspensions, emulsions, percutaneous absorption preparations, suppositories, ointments, lotions, inhalants, injections and the like. The crystals and the lyophilized compositions of the present invention as well as said medicinal preparation may be orally or parenterally administered (such as intravenous administration, intramuscular administration, intraperitoneal administration, percutaneous administration, intratracheal administration, intracutaneous administration, or subcutaneous administration).

In said medicinal preparation of the present invention, in addition to compound (I), a β-lactamase inhibitor, β-lactam antibiotics may be incorporated. Examples of what may be incorporated include piperacillin, ampicillin, benzylpenicillin, cefoperazone, cefazolin, cefalotin, cefotiam, cefminox, cefmetazole, flomoxef, cefodizime, cefotaxime, ceftriaxone, cefmenoxime, latamoxef, ceftazidime, cefepime, cefozopran, cefpirome, aztreonam, imipenem, doripenem, panipenem, biapenem, meropenem, and their pharmacologically acceptable salts and solvates.

Any additive that can generally be added to injections may, where appropriate, be incorporated in said injections of the present invention. Examples of what may be incorporated for the purpose of adjusting pH include inorganic acids such as hydrochloric acid and phosphoric acid, and salts thereof, organic acids such as citric acid, malic acid, tartaric acid, and succinic acid, and salts thereof, amino acids such as arginine, alanine, aspartic acid, histidine, and glycine, and bases such as sodium hydroxide and sodium bicarbonate. Examples of what may be incorporated for the purpose of adjusting osmotic pressure include glucose, mannitol, xylitol, sorbitol, sucrose, lactose, maltose, trehalose, and dextran. Furthermore, examples of what may be incorporated for the purpose of improving solubility include polyols such as polyethylene glycol and glycerin, and surfactants such as polysorbates, sorbitan sesquioleate, polyoxyethylene-polyoxypropylene glycols, and polyoxyethylene hydrogenated castor oils.

EXAMPLES

The following Examples and Comparative examples describe embodiments of the present invention in concrete terms, but are not to be construed as limiting the present invention.

Example 1

A Lyophilized Composition of Compound (I)

Example 1a 700 mg of compound (I) and 126.1 mg of sodium chloride were dissolved into distilled water, and the total weight was adjusted to 7 g. The solution was filtered through a 0.20-μm membrane filter (MILLEX (trademark) LG SLLGH13NH; Merck Millipore) and placed in an amount of 1 g into a 5-mL glass vial, and then half stoppering was performed with a rubber top. The vial filled with the solution was set inside a lyophilizer (DFM-05B-S; ULVAC) and cooled under atmospheric pressure for 1 hour, with the shelf temperature of the lyophilizer set to 5° C. Afterward, the shelf temperature of the lyophilizer was lowered to −40° C. over a 1 hour period, thereby causing the solution to freeze, and this temperature was maintained for 3 hours. Subsequently, the pressure inside the lyophilizer was set to approximately 10 Pa, and the shelf temperature of the lyophilizer was raised to −10° C. over a 6 hour period, after which this state was maintained for 30 hours. The pressure inside the lyophilizer was then set below 10 Pa, the shelf temperature of the lyophilizer was raised to 25° C. over a 7 hour period, and this state was maintained for 15 hours. After completion of drying, the pressure inside the lyophilizer was reverted to atmospheric pressure using nitrogen gas, and full stoppering was performed with a rubber top. The vial was taken out of the lyophilizer, and an aluminum cap was screwed on to obtain a lyophilized composition in which compound (I) is crystalline form I. It may be added that the sodium chloride used was of special grade and was purchased from Nacalai Tesque.

Example 1b 600 mg of compound (I) and 129.7 mg of sodium chloride were dissolved into distilled water, and the total weight was adjusted to 6 g. The solution was filtered through a 0.20-μm membrane filter (MILLEX (trademark) LG SLLGH13NH; Merck Millipore) and placed in an amount of 1 g into a 5-mL glass vial, and then half stoppering was performed with a rubber top. The vial filled with the solution was set inside a lyophilizer (Console 12-3-ST-CR; VirTis) and cooled under atmospheric pressure for 1 hour, with the shelf temperature of the lyophilizer set to 5° C. Afterward, the shelf temperature of the lyophilizer was lowered to −40° C. over a 2.5 hour period, thereby causing the solution to freeze, and this temperature was maintained for 1 hour. Subsequently, the shelf temperature of the lyophilizer was raised to −4° C. over a 0.5 hour period, and this temperature was maintained for 15 hours. The shelf temperature of the lyophilizer was then lowered to −40° C. over a 2 hour period, thereby causing the solution to freeze again, and this temperature was maintained for 0.5 hours. Subsequently, the pressure inside the lyophilizer was set below 10 Pa, the shelf temperature of the lyophilizer was raised to −10° C. over a 0.5 hour period, and this state was maintained for 20 hours. The shelf temperature of the lyophilizer was then raised to 25° C. over a 0.5 hour period, and this state was maintained for 3 hours. After completion of drying, the pressure inside the lyophilizer was reverted to atmospheric pressure and full stoppering was performed with a rubber top. The vial was taken out of the lyophilizer, and an aluminum cap was screwed on to obtain a lyophilized composition in which compound (I) is crystalline form I.

Example 2

Crystalline form I of Compound (I)

Example 2a 1.0 g of crystalline form III of compound (I) was dissolved in 10 mL of deionized water. 0.18 g of sodium chloride was added to the obtained solution and dissolved therein at ambient temperature. This solution was cooled to 0° C. and then finely filtered. To the filtrate was added dropwise 45 mL of chilled isopropanol for over 1 hour, followed by stirring overnight. The resulted crystals were isolated, and dried under reduced pressure at ambient temperature for 0.5 hour to afford 0.82 g of crystals of compound (I) (yield=82.0%, crystalline form I).

Example 2b

After dissolving 1.71 g of sodium chloride in 100 mL of deionized water, 10 g of compound (I) was added and dissolved at ambient temperature. This solution was cooled to 0 to 5° C. and finely filtered. Then, to the filtrate 50 mg (0.5 wt %) of crystalline form I of compound (I) obtained in Example 2a was added and stirred for 1 hour at 0 to 5° C. 500 mL of chilled isopropanol was added dropwise for over 1 hour, stirred overnight, and then crystals were isolated. The obtained crystals were dried under reduced pressure at ambient temperature for 0.5 hour to afford 9.53 g of crystals of compound (I) (yield=94.8%, crystalline form I).

Comparative Example 1

A Lyophilized Composition of Compound (I)

This comparative example was prepared using the same procedure as Example 1 except that no sodium chloride was incorporated. Specifically, 700 mg of compound (I) was dissolved into distilled water, and the total weight was adjusted to 7 g. The solution was filtered through a 0.20-μm membrane filter (MILLEX (trademark) LG SLLGH13NH; Merck Millipore) and placed in an amount of 1 g into a 5-mL glass vial, and then half stoppering was performed with a rubber top. The vial filled with the solution was set inside a lyophilizer (DFM-05B-S; ULVAC) and cooled under atmospheric pressure for 1 hour, with the shelf temperature of the lyophilizer set to 5° C. Afterward, the shelf temperature of the lyophilizer was lowered to −40° C. over a 1 hour period, thereby causing the solution to freeze, and this temperature was maintained for 3 hours. Subsequently, the pressure inside the lyophilizer was set to approximately 10 Pa, the shelf temperature of the lyophilizer was raised to −10° C. over a 6 hour period, and this state was maintained for 30 hours. The pressure inside the lyophilizer was then set below 10 Pa, the shelf temperature of the lyophilizer was raised to 25° C. over a 7 hour period, and this state was maintained for 15 hours. After completion of drying, the pressure inside the lyophilizer was reverted to atmospheric pressure using nitrogen gas, and full stoppering was performed with a rubber top. The vial was taken out of the lyophilizer, and an aluminum cap was screwed on to obtain a lyophilized composition in which compound (I) is amorphous.

Comparative Example 2

Crystalline Form I of Compound (I) (a Producing Method Using an Octadecylsilica Gel or Resin Column Purification)

Comparative Example 2a

A 0.5 M acetate buffer (pH 5.5, 35 mL) was ice-cooled, and to this were added compound (I) (36 g) and cooled 5M aqueous sodium hydroxide solution alternately to adjust the pH to 5.5. The mixture was subjected to octadecylsilica gel column chromatography (3.6 L) and eluted with water. Active fractions were collected and concentrated under reduced pressure with a water bath of 35° C. The precipitated crystals were dried in vacuo overnight. 2.10 g of the resulting crystals was pulverized, and then isopropanol/water (19/1, 13 mL) was added under ice-cooling, followed by stirring at 0° C. for 1 hour. The suspension was filtered, followed by washing with cooled isopropanol/water (19/1, 80 mL). The resulting crystals were dried in vacuo to afford 1.68 g of crystalline form I of compound (I) (yield 80%). DSC endothermic peak: 111° C. Solubility in an aqueous 60% isopropanol solution: 0.44% (10° C.), 0.48% (20° C.).

Comparative Example 2b

Compound (I) (net 4.253 g) was dissolved in a 0.2 M phosphate buffer (pH 6.5, 73 mL) and the pH was adjusted to 5.5, followed by dilution with water (20 mL). The mixture was concentrated to 130 mL, subjected to resin purification (SP207, 260 mL), and eluted with water (238 mL) and an aqueous 10% isopropanol solution (780 mL). Active fractions were collected and concentrated to 30 mL under reduced pressure. To this was introduced activated carbon (Seisei Shirasagi, 87 mg), followed by stirring at room temperature for 30 minutes. The activated carbon was filtered off with a membrane filter, and the filtrate was subjected to lyophilization to afford 4.07 g of compound (I) in an amorphous form (yield 95.7%). This amorphous compound (I) (0.2 g) was dissolved in water (0.8 mL), and the solution was added isopropanol (1.2 mL) and seeded with crystalline form I (Comparative example 2a, 1 mg) at room temperature, followed by stirring with a stirring bar for 3 hours. The precipitated crystals were filtered and dried to afford 0.1 g of crystalline form I of compound (I) (yield 50%).

Comparative Example 2c

Compound (I) (net 2.113 g) and a 0.2 M phosphate buffer (pH 6.5, 73 mL) were added alternately, and the pH was adjusted to 4.6, followed by dilution with water (27 mL). The mixture was concentrated to 80 mL under reduced pressure, and then the pH was adjusted to 5.4 with a 0.2 M phosphate buffer (pH 6.5, 16 mL), followed by dilution with water (48 mL). The mixture was subjected to resin purification (SP207, 240 mL), and eluted with water (276 mL) and an aqueous 10% isopropanol solution (720 mL). Active fractions were collected and concentrated under reduced pressure to 12 mL. To this was added activated carbon (Seisei Shirasagi, 40 mg), followed by stirring at room temperature for 30 minutes. The activated carbon was filtered off through a membrane filter, followed by dilution with water to 14 mL. The aqueous solution was seeded with crystalline form I (Example 2b, 6 mg), stirred with a stirring bar at room temperature. To the resulting suspension was added dropwise isopropanol (84 mL) over 1 hour. After completion of dropwise addition, the mixture was stirred for 3 hours. The precipitated crystals were filtered and dried to afford 1.834 g of crystalline form I of compound (I) (yield 86.8%). Water content: 5.37%, the content of anhydrous product: 95.3%, HPLC area ratio of 99.3%.

Test Example 1

Powder X-ray Diffraction Measurements

Powder X-ray diffraction measurements were performed for the lyophilized compositions obtained in Example 1a, Example 1b and Comparative example 1, the crystals obtained in Example 2a and Example 2b, the crystals obtained in Comparative Example 2a, Comparative Example 2b and Comparative Example 2c, and sodium chloride using a powder X-ray diffractometer (RINT2200; Rigaku), under the following conditions.
<Measurement Conditions>
X-ray: Cu (40 kV, 40 mA)
Sample rotation: 60 rpm
Divergence slit: 0.5°
Scattering slit: 0.5°
Receiving slit: 0.3 mm
Monochromator receiving slit: 0.8 mm
Sampling width: 0.02°
Detector: scintillation counter
Scanning speed: 1°/min
Scanning range: 5°-40°

Figure 2:
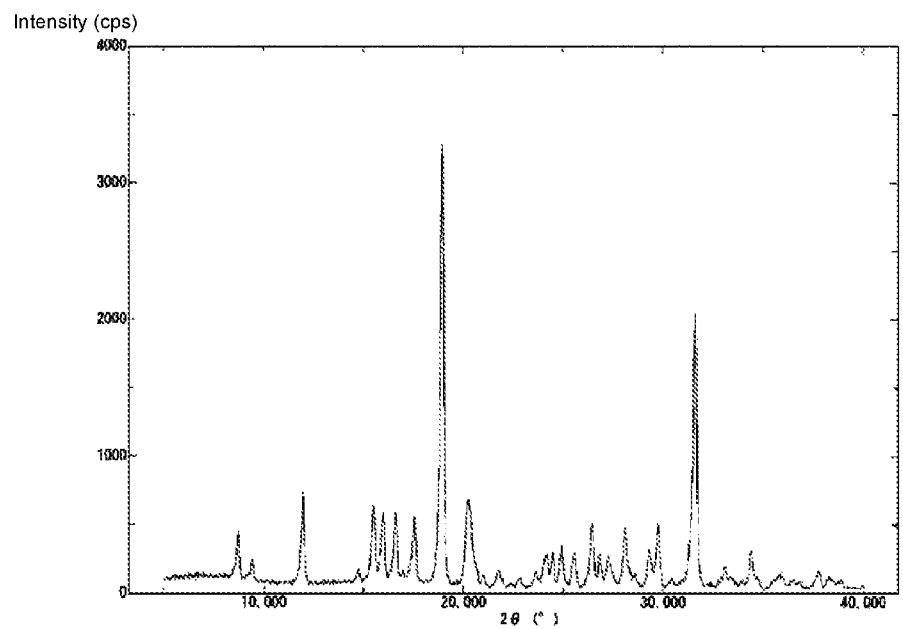
FIG. 2 Powder X-ray diffractogram of the lyophilized composition obtained in Example 1b.
Figure 3:
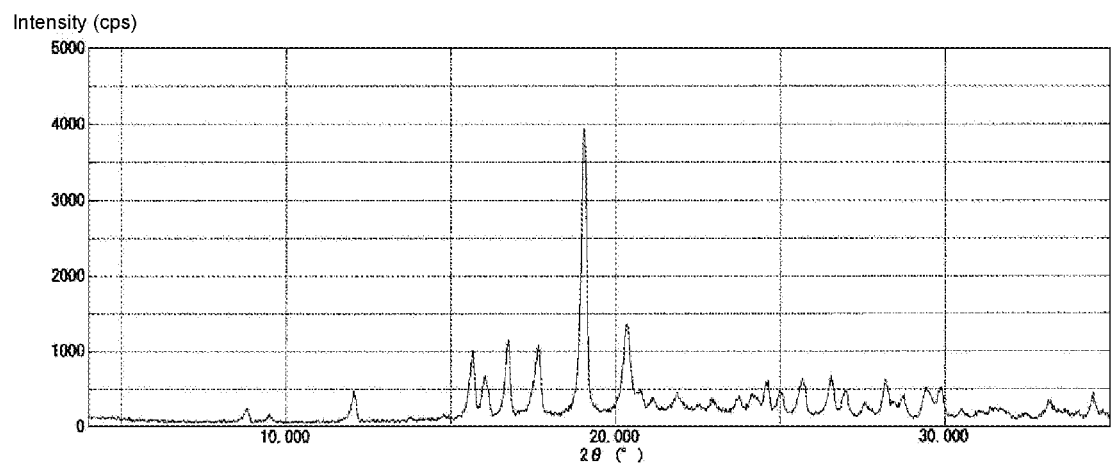
FIG. 3 Powder X-ray diffractogram of the crystals obtained in Example 2b.
Figure 4:
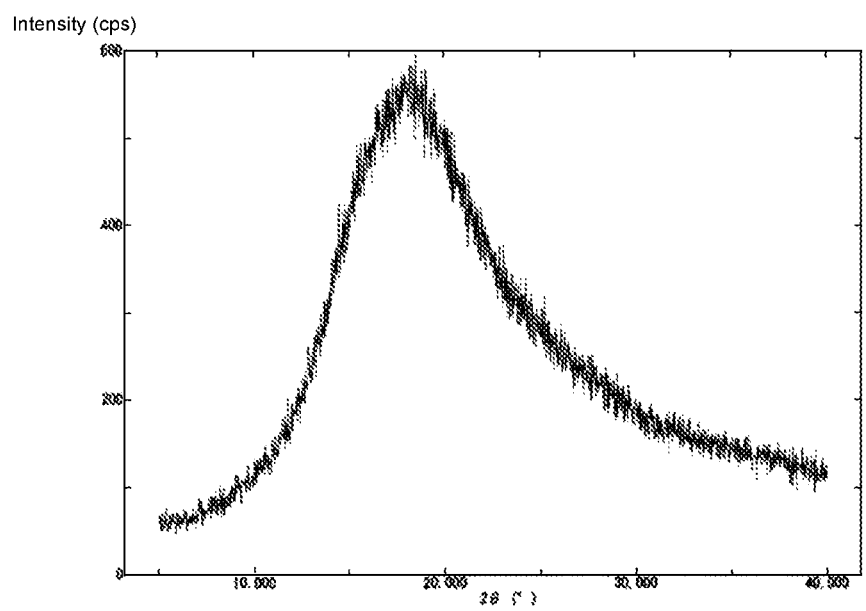
FIG. 4 Powder X-ray diffractogram of the lyophilized composition obtained in Comparative example 1.
Figure 5:
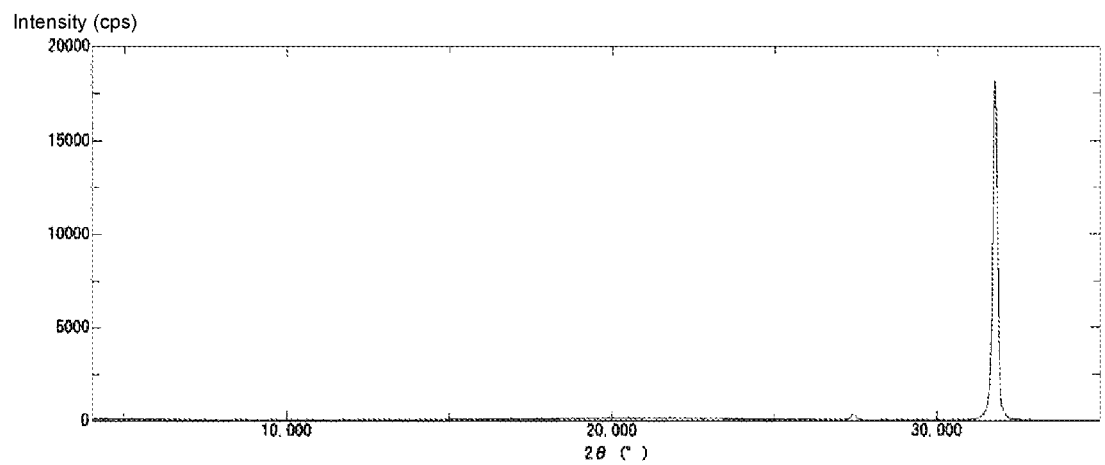
FIG. 5 Powder X-ray diffractogram of sodium chloride.

The X-ray diffractograms for Example 1a, Example 1b, Example 2b, Comparative example 1 and sodium chloride are shown in FIGS. 1, 2, 3, 4 and 5, respectively. The lyophilized compositions obtained in Examples 1a and 1b were crystalline while the lyophilized composition obtained in Comparative example 1 was amorphous. Further, it was confirmed that the crystals of Example 2b were crystalline form I of compound (I) in view of the X-ray diffractgram thereof. Likely, it was confirmed that the crystals of Example 2a and Comparative examples 2a to 2c were also crystalline form I of compound (I) in view of the X-ray diffractograms thereof, but the data were not shown.

Considering that the same crystalline form I of compound (I) were obtained in any of Examples 2a and 2b as well as Comparative examples 2a to 2c, it was demonstrated that crystalline form I can be predominantly produced by crystallization from an aqueous solution containing sodium chloride without passing through purification with octadecylsilica gel column chromatography or resin performed in Comparative examples 2a to 2c.

A peak was observed at 31 to 32° in the X-ray diffractograms for Examples 1a and 1b, but the peak was absent in Example 2b. Considering that a peak was observed at 31 to 32° in the X-ray diffractogram for sodium chloride (FIG. 5), it is understood that this peak was caused by sodium chloride contained in the lyophilized compositions. Since an aqueous solution containing compound (I) and an inorganic salt is lyophilized in the present invention, the obtained lyophilized composition obviously contains the inorganic salt. Since the pattern except the peak at 31-32° of the X-ray diffractogram for Examples 1a and 1b matches the pattern of Example 2b, it was confirmed that crystals obtained in Examples 1a and 1b were also crystalline form I. On the other hand, after checking amounts of sodium ion and chloride ion contained in crystalline form I obtained in Example 2b with ion chromatography, both of the amounts were 0.1% or less.

In the present invention, although compound (I) is crystallized from an aqueous solution containing compound (I) and an inorganic salt, it was confirmed that the obtained crystals of compound (I) does not contain the inorganic salt.

Test Example 2

Stability Evaluation

The crystals obtained in Examples 1a and 1b, and the amorphous lyophilized composition obtained in Comparative example 1 were subjected to stress tests at 60° C. (2 weeks and 1 month) using a temperature and humidity test chamber (LH2O-12M; Nagano Science), and then related substances were measured by HPLC under the following conditions.
<Testing Conditions>
Column: Waters Atlantis dC18, 5 µm, 4.6×250 mm
Column temperature: maintained constant at about 35° C.
Injection volume: 5 µL
Detector: UV absorption photometer (Measured wavelength: 210 nm)
Mobile phase A: 1.32 g of diammonium hydrogen phosphate was dissolved into 900 mL of water, to which was added phosphoric acid to adjust the pH to 3.0, and the total volume was adjusted to 1000 mL with water.
Mobile phase B: acetonitrile for liquid chromatography
Gradient program: The mixing ratio of mobile phases A and B was controlled to change in the following manner.

| Time after injection (min) | Mobile phase A (vol %) | Mobile phase B (vol %) |
| --- | --- | --- |
| 0-5 | 100 | 0 |
| 5-20 | 100 → 90 | 0 → 10 |
| 20-30 | 90 | 10 |

Flow rate: 1.0 mL/min
Retention time of compound (I): Approximately 6.5 min
Measurement time: 30 min Changes in the total amount of related substances for each sample were shown in Table 2. The crystalline lyophilized compositions contained lower amounts of related substances in the initial state than the amorphous lyophilized composition. Moreover, there was, after the stress tests, a considerable increase in the amount of related substances present in the amorphous lyophilized composition, whereas increases in the amounts of related substances were lower for the crystalline lyophilized compositions. These results confirmed that turning compound (I) into a crystalline lyophilized composition using a method of the present invention produces a marked improvement in storage stability.

TABLE 2

| | | Total amount of related substances (%) | | |
|---|---|---|---|---|
| | Crystallinity | Initial state | 60° C. 2 weeks | 60° C. 1 month |
| Example 1a | Crystalline | 0.25 | 1.30 | 0.98 |
| Example 1b | Crystalline | 0.30 | 0.50 | 0.55 |
| Comparative example 1 | Amorphous | 0.56 | 15.07 | 24.54 |

Reference Example 1

Method for Producing Compound (I)

Reference Example 1a tert-Butyl{2-[({[(2S,5R)-6-benzyloxy-7-oxo-1,6-diazabicyclo[3.2.1]oct-2-yl]carbonyl}amino)oxy]ethyl}carbamate

[Chemical formula 2]

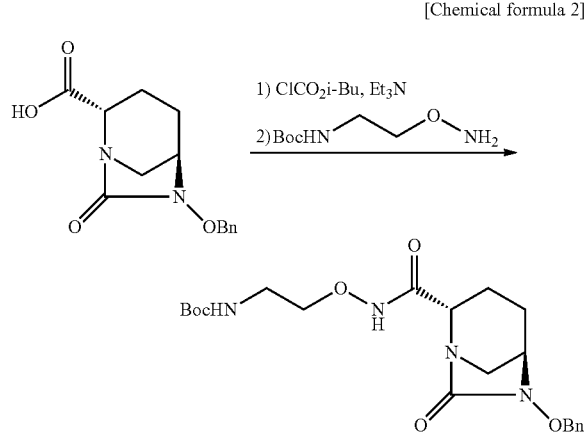

A solution of (2S,5R)-6-(benzyloxy)-7-oxo-1,6-diazabicyclo[3.2.1]octane-2-carboxylic acid (4.80 kg, 17.373 mol) in dehydrated ethyl acetate (62 L) was cooled to −30° C., to which isobutyl chloroformate (2.52 kg) and then triethylamine (1.85 kg) were added dropwise, and was stirred at −30° C. for 15 minutes. To the reaction mixture was added a solution of tert-butyl 2-(aminooxy)ethylcarbamate in dehydrated ethyl acetate (15 wt %, 23.45 kg) over 30 minutes (the residue washed with 2 L of dehydrated ethyl acetate), and the temperature was raised to 0° C. over 1 hour. The mixture was washed sequentially with an 8% solution of citric acid (65 L), a 5% solution of sodium bicarbonate (60 L), and water (60 L), and concentrated to 24 L. A step of adding ethyl acetate (24 L) to the concentrated mixture, followed by concentration to 24 L for solvent displacement was performed twice, and to the resultant concentrated solution, ethyl acetate (29 L) and hexane (72 L) were added, and stirred overnight. To the mixture, hexane (82 L) was added dropwise and stirred for 2 hours. The precipitated crystals were separated by filtration, washed with hexane, and vacuum-dried to give 5.51 kg of the title compound (yield 76%).

HPLC:COSMOSIL 5C18 MS-II 4.6×150 mm, 33.3 mM phosphate buffer/MeCN=50/50, 1.0 mL/min, UV 210 nm, RT 4.4 min; $^1$H NMR (400 MHz, CDCl$_3$) δ 1.44 (s, 9H), 1.56-1.70 (m, 1H), 1.90-2.09 (m, 2H), 2.25-2.38 (m, 1H), 2.76 (d, J=11.6 Hz, 1H), 3.03 (br. d., J=11.6 Hz, 1H), 3.24-3.47 (m, 3H), 3.84-4.01 (m, 3H), 4.90 (d, J=11.6 Hz, 1H), 5.05 (d, J=11.6 Hz, 1H), 5.44 (br. s., 1H), 7.34-7.48 (m, 5H), 9.37 (br. s., 1H); MS m/z 435 [M+H]$^+$.

Reference Example 1b tert-Butyl {2-[({[(2S,5R)-6-hydroxy-7-oxo-1,6-diazabicyclo[3.2.1]oct-2-yl]carbonyl}amino)oxy]ethyl}carbamate

[Chemical formula 3]

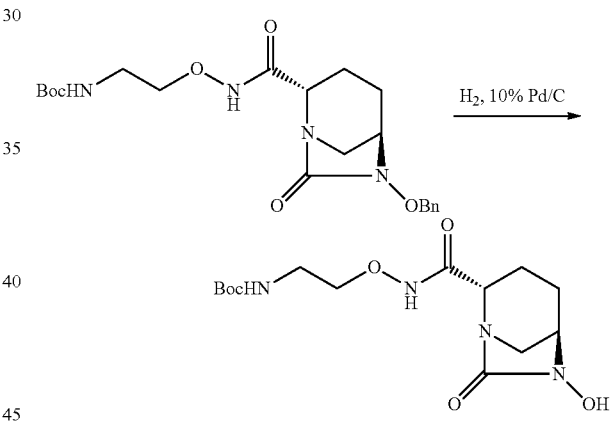

To a solution of tert-butyl {2-[({[(2S,5R)-6-benzyloxy-7-oxo-1,6-diazabicyclo[3.2.1]oct-2-yl]carbonyl}amino)oxy]ethyl}carbamate (5.52 kg, 12.705 mol) in methanol (85 L), a 10% palladium-carbon catalyst (50% water, 0.55 kg) was added and stirred under hydrogen pressure (0.1 MPa) for 1 hour. The catalyst was filtered off and the solid was washed with methanol (25 L). The filtrate and wash were combined and concentrated under reduced pressure to 39 L at a solution temperature below 10° C. A step of adding acetonitrile (44 L) to the concentrated mixture, followed by concentration to 39 L at a solution temperature below 10° C. for solvent displacement was performed twice, and the mixture was cooled to 0° C. and stirred overnight. The precipitated crystals were separated by filtration, washed with acetonitrile (24 L), and vacuum-dried to give 3.63 kg of the title compound (yield 83%).

HPLC:COSMOSIL 5C18 MS-II 4.6×150 mm, 33.3 mM phosphate buffer/MeCN=75/25, 1.0 mL/min, UV 210 nm, RT 3.9 min; $^1$H NMR (400 MHz, CD$_3$OD) δ 1.44 (s, 9H), 1.73-1.83 (m, 1H), 1.86-1.99 (m, 1H), 2.01-2.12 (m, 1H), 2.22 (br. dd., J=15.0, 7.0 Hz, 1H), 3.03 (d, J=12.0 Hz, 1H), 3.12 (br. d., J=12.0 Hz, 1H), 3.25-3.35 (m, 2H), 3.68-3.71 (m, 1H), 3.82-3.91 (m, 3H); MS m/z 345 [M+H]$^+$.

Reference Example 1c

Tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}carbamate

[Chemical formula 4]

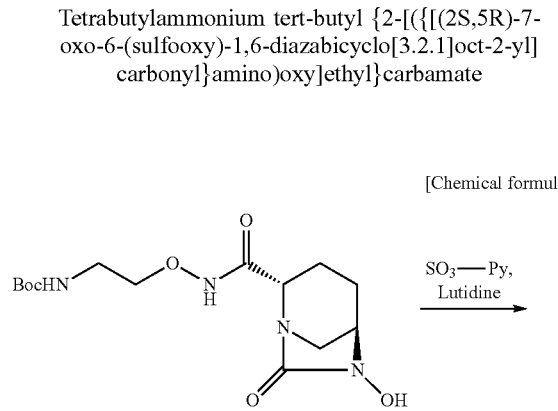

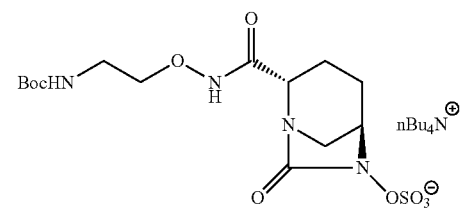

To acetonitrile (51 L) were sequentially added water (51 mL), tert-butyl {2-[({[(2S,5R)-6-hydroxy-7-oxo-1,6-diazabicyclo[3.2.1]oct-2-yl]carbonyl}amino)oxy]ethyl}carbamate (3.53 kg, 10.251 mol), sulfur trioxide-pyridine complex (3.95 kg), and 2,6-lutidine (2.21 kg), and stirred at 35 to 45° C. overnight. The mixture was filtered to remove the insoluble matter, the solid was washed with acetonitrile (11 L) and the filtrate and wash were combined and concentrated to 17 L. The concentrated solution was cooled to below 10° C., to which were added a 9% aqueous solution of sodium dihydrogenphosphate (60 L) and ethyl acetate (113 L) to effect phase separation, and the organic layer was extracted again with a 9% aqueous solution of sodium dihydrogenphosphate (11 L). To the aqueous layer obtained were added ethyl acetate (113 L), a 30% aqueous solution of tetrabutylammonium hydrogen sulfate (12.87 kg), and a 37% aqueous solution of sodium dihydrogenphosphate (56.5 kg), and stirred for 15 minutes. The organic layer was separated, washed with a 20% aqueous solution of sodium dihydrogenphosphate (60 L), dried over anhydrous magnesium sulfate (2.5 kg), filtered, and then concentrated under reduced pressure. Crystals of the title compound deposited in the concentrated solution were dissolved into ethyl acetate, and the total volume was adjusted to 20 L to yield 32.55 kg of a solution of the title compound in ethyl acetate (net 6.25 kg, yield 92%). This solution was used in the next step without further purification.

Reference Example 1d

Crude Compound (I)

[Chemical formula 5]

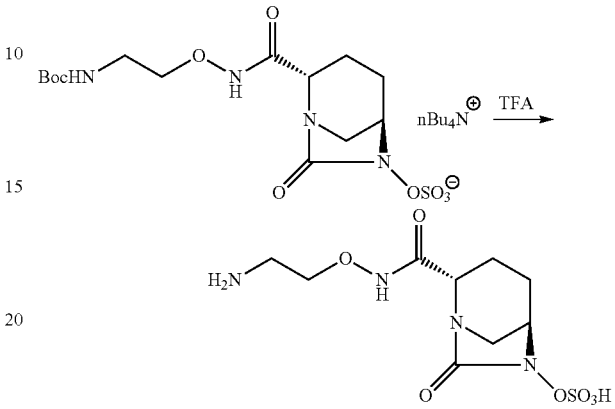

A solution of tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}carbamate (788 g, net 467.1 g, 0.701 mol) in dichloromethane (934 mL) was cooled to −20° C. in a nitrogen stream, to which trifluoroacetic acid (934 mL) was added dropwise over 15 minutes, and the temperature was raised to 0° C., followed by stirring for 1 hour. The reaction mixture was cooled to −20° C., to which diisopropyl ether (4.17 L) was added dropwise, after which the temperature of the mixture was raised to −6° C., followed by stirring for 1 hour. The precipitate was filtered, washed by suspension in diisopropyl ether (2×1 L), and the wet solid was vacuum-dried to give 342.08 g of the title compound (net 222.35 g, yield 98%, HPLC area ratio 96.1%, CE/TFA 27 mol %).

Reference Example 1e 0.2 M phosphate buffer (pH 6.5, 7.2 L) was cooled to below 10° C., to which (2S,5R)—N-(2-aminoethoxy)-7-oxo-6-(sulfooxy)-1,6-diazabicyclo[3.2.1]octane-2-carboxamide (the crude compound (I) in Reference example 1d, net 1.2 kg) and ice-cold 0.2 M phosphate buffer (pH 6.5, 3.5 L) were added alternately portionwise while stirring in a manner in which the pH remained between 4.2 and 4.8, and the final pH was adjusted to 4.6. The mixture was diluted with water (19.3 L) (total quantity 30 L), and concentrated to 24 L under reduced pressure at solution temperatures below 18° C. After the pH of the concentrated solution was adjusted to 5.4 with 0.2 M phosphate buffer (pH 6.5, 2.4 L), the concentrated solution was diluted with water to 43.2 L and purified using a resin (Sepabeads SP207, 75 L), where water (83 L) and a 10% aqueous solution of isopropanol were used for elution and active fractions were collected. The active fractions were combined (33 L), concentrated to 7.2 L at solution temperatures below 15° C., to which was added activated carbon (24 g), followed by stirring for 30 minutes. The activated carbon was filtered off through a membrane filter, and washed with water (0.4 L×2). The filtrate and wash were combined and after the temperature of the solution was adjusted to 20 to 25° C., crystalline form III (3.6 g) obtained according to a method mentioned in Example 7a of Patent Document 6 were inoculated. To the mixture, isopropanol (50.4 L) was added dropwise over 1 hour, and stirred overnight. The crystals deposited were filtered, washed with isopropanol (4.8 L) and vacuum-dried until the temperature of the wet crystals reached 20° C., to yield 1.17 kg of crystalline form III of compound (I) (yield 90%).

INDUSTRIAL APPLICABILITY

According to the present invention, crystals, especially a single crystalline form, and in particular stable crystalline form I of compound (I) can be produced easily in an industrial scale, and further the present invention provides a lyophilized composition of compound (I), and especially a single crystalline form and in particular crystalline form I thereof, having good storage stability and therefore provides a useful method for producing injections and the like of compound (I).

The invention claimed is:

1. A process for producing crystals of a compound represented by the following formula (I):

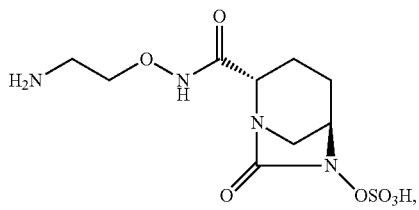

comprising crystallizing the compound from an aqueous solution containing the compound and an inorganic salt, without previous purification of the compound with a column,
  wherein a crystalline form I of the compound having characteristic peaks appearing at a lattice spacing (d) of 7.34, 5.66, 5.53, 5.30, 5.02, 4.66, 4.37, 4.28, 4.06, 3.68, 3.62, 3.47, 3.36, 3.30, 3.16, 3.11, 3.03, 2.99 and 2.50 Å in a powder X-ray diffraction pattern is produced.

2. A process for producing crystals of a compound represented by the following formula (I):

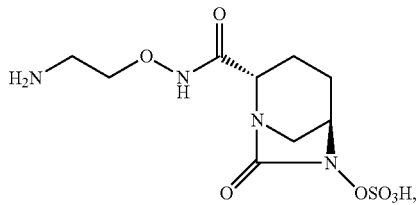

comprising crystallizing the compound from an aqueous solution containing the compound and an inorganic salt, without previous purification of the compound with a column,
  wherein the aqueous solution containing the compound and an inorganic salt is obtained by dissolving the compound and the inorganic salt together in water, or by dissolving either of the compound or the inorganic salt in water and then dissolving the other in the resultant solution, and
  wherein a crystalline form I of the compound having characteristic peaks appearing at a lattice spacing (d) of 7.34, 5.66, 5.53, 5.30, 5.02, 4.66, 4.37, 4.28, 4.06, 3.68, 3.62, 3.47, 3.36, 3.30, 3.16, 3.11, 3.03, 2.99 and 2.50 Å in a powder X-ray diffraction pattern is produced.

3. A process for producing crystals of a compound represented by the following formula (I):

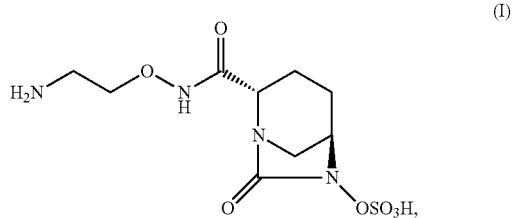

comprising crystallizing the compound from an aqueous solution containing the compound and an inorganic salt, without previous purification of the compound with a column,
  wherein the compound is crystallized by adding a poor solvent to the aqueous solution containing the compound and the inorganic salt, and
  wherein a crystalline form I of the compound having characteristic peaks appearing at a lattice spacing (d) of 7.34, 5.66, 5.53, 5.30, 5.02, 4.66, 4.37, 4.28, 4.06, 3.68, 3.62, 3.47, 3.36, 3.30, 3.16, 3.11, 3.03, 2.99 and 2.50 Å in a powder X-ray diffraction pattern is produced.

4. The process according to claim 3, wherein the poor solvent is an alcohol.

5. The process according to claim 1, wherein the compound is crystallized by subjecting the aqueous solution containing the compound and the inorganic salt to lyophilization.

* * * * *